(12) United States Patent
Popov et al.

(10) Patent No.: US 8,560,265 B2
(45) Date of Patent: Oct. 15, 2013

(54) METHOD AND DEVICE FOR DETERMINATION OF THERMAL PROPERTIES OF SOLID BODIES

(75) Inventors: Yury Anatolyevich Popov, Moscow (RU); Valery Vasil'evich Shako, Domodedova (RU); Anton Vladimirovich Parshin, Moscow (RU); Sergey Sergeevich Safonov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 460 days.

(21) Appl. No.: 12/909,104

(22) Filed: Oct. 21, 2010

(65) Prior Publication Data
US 2011/0106485 A1 May 5, 2011

(30) Foreign Application Priority Data
Oct. 21, 2009 (RU) .................................. 2009138616

(51) Int. Cl.
*G01K 17/00* (2006.01)
*G01F 1/12* (2006.01)

(52) U.S. Cl.
USPC ........... 702/136; 702/100; 702/137; 702/182; 702/183

(58) Field of Classification Search
USPC .................... 702/183–189, 98–100, 136–140
See application file for complete search history.

(56) References Cited

U.S. PATENT DOCUMENTS

| | | | |
|---|---|---|---|
| 3,672,205 A | * | 6/1972 | Leidenfrost .................... 374/44 |
| 4,933,887 A | * | 6/1990 | Danko et al. .................. 702/136 |
| 5,044,767 A | | 9/1991 | Gustafsson |

FOREIGN PATENT DOCUMENTS

| | | |
|---|---|---|
| DE | 102004022206 | 12/2005 |
| RU | 2190209 | 9/2002 |
| RU | 2212653 | 9/2003 |

OTHER PUBLICATIONS

Combined Search and Examination Report of British Application No. GB1017740.0 dated Jan. 25, 2011: pp. 1-3.
Kiyohashi et al., "Development of Direct Measurement Method for Thermophysical Properties of Reservoir Rocks in Situ by Well Logging," Proceedings World Geothermal Congress, 2000: pp. 2665-2670.

* cited by examiner

*Primary Examiner* — Phuong Huynh

(57) ABSTRACT

The invention relates to the area of thermophysical studies of media and is intended for the determination of thermal properties of solid media by placing a measuring device on the surface of the medium. A heater, which is made in the form of a flexible membrane capable of taking the shape of the solid body surface under the action of the hold-down pressure and which additionally serves as a temperature sensor, is pressed to the solid body surface by using a hold-down element in such a way as to ensure that the heater shape fits the shape and irregularities of the solid body surface. The heater temperature is registered throughout the heater surface during and after the heating. The thermal conductivity and thermal diffusivity of the solid body are determined by processing the heater temperature measurement data both in the time range from the start of the solid body heating to the start of the thermal convention of the ambient medium and after the termination of the solid body heating process.

16 Claims, 1 Drawing Sheet

METHOD AND DEVICE FOR DETERMINATION OF THERMAL PROPERTIES OF SOLID BODIES

FIELD OF THE INVENTION

Figure 1:
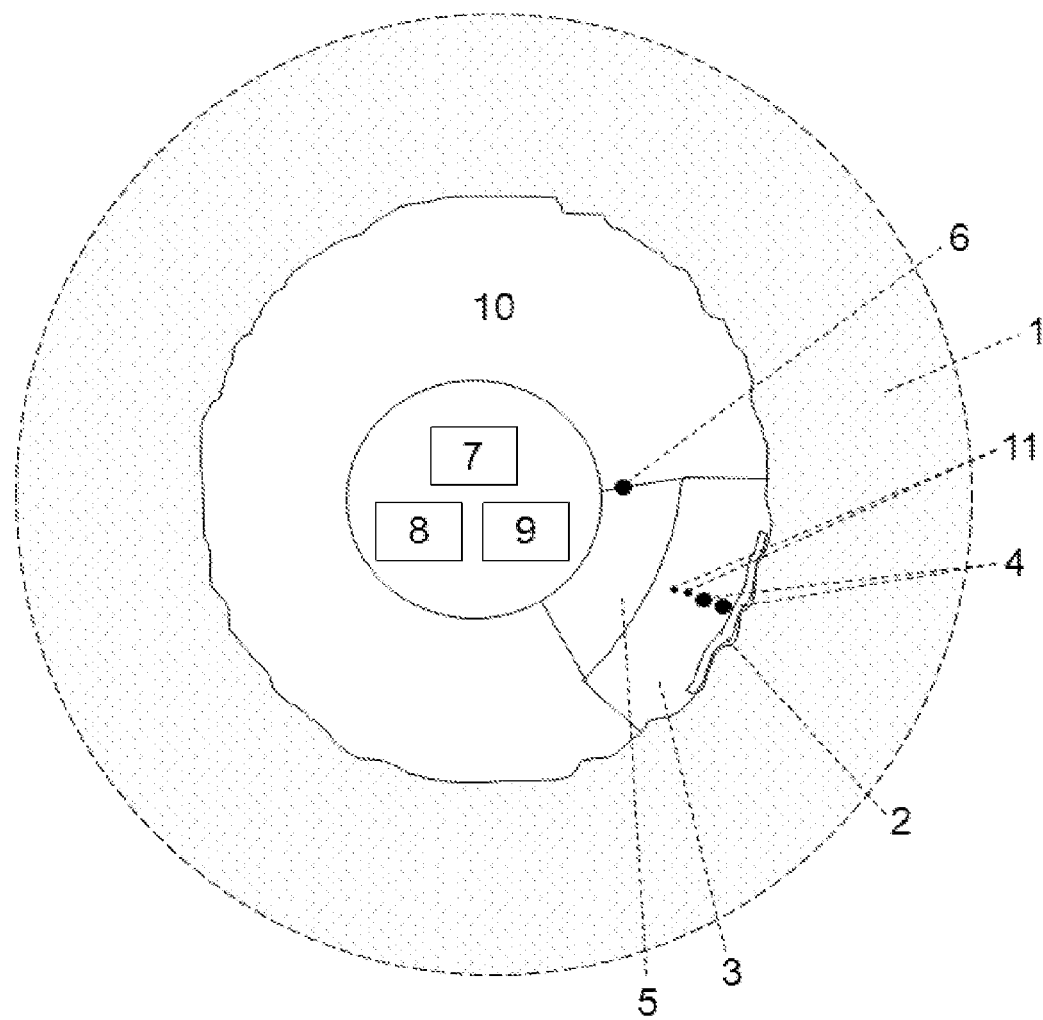

The invention relates to the field of thermophysical studies of media, namely, to the determination of thermal properties of solid bodies by placing a measuring device on the surface of the medium. Such measurements can be exemplified by the determination of the thermal conductivity and thermal diffusivity of rock in situ, which is done by placing a measuring device into wells, either cased or uncased. In the latter instance, such measurements are used, for example, for the enhancement of the efficiency of the oil-and-gas field development and geothermal field development.

The invention suggests a method for determination of thermal properties (specifically, the thermal conductivity and the thermal diffusivity) of solid bodies by measuring the time changes in the temperature of the medium under study when exposed to a thermal energy source, and a device for the implementation of this method.

BACKGROUND OF THE INVENTION

There is a known method for determination of thermal properties of solid materials, which is described in RF patent No. 2212653 and includes the pulse heating of a solid body, measurements of the solid body temperature on the solid body surface, and the processing of the electronic signal of the solid body temperature. The main disadvantage of the known method consists in the fact that complicated processing of measurement data is required in case of the pulse heating, which reduces the measurement accuracy and increases considerably the measurement cost.

The closest analogue of the suggested method is the method for determination of thermal properties of solid materials, which is described in the article "Flat Sonde Method for Determination of Thermal Properties of Rock in Wells and Mines" by P. I. Filippov, in the book "Methods for Determination of Thermal Properties of Rock", Moscow, Nauka Publishing House, 1970, pages 107-111. The known method includes the heating of the solid body surface by a flat heater restricted by a heat insulator from one side, the registration of the heater temperature during the heating, and the determination of the thermal conductivity and thermal diffusivity of the solid body, based on the heater temperature data. However, this method has serious disadvantages which limit its area of application. These disadvantages include a low accuracy of measurements taken on cylindrical, conical, spherical, elliptical, rough and irregular surfaces, as well as in wells filled with fluid. These disadvantages result from the fact that the heater temperature is registered not on the entire heater surface in contact with the solid body, but only in the small area where a point temperature sensor is located, and that it is impossible to achieve the required thermal contact of the heater and the temperature sensor with the solid body throughout the heater surface and the temperature sensor surface. The measurement process is limited by the heater's operating period only, and it is impossible to take into account the heat loss from the heater into the adjacent heat insulator, which is necessary for the registration of the changes in the contact thermal resistance between the heater and the solid body surface. A serious disadvantage consists in the fact that the measurement data may be considerably distorted due to the effect of the thermal convection (which is inevitable in case of a heat source present in the well fluid), and that the equation used as an algorithm for processing the signal and for converting the signal into the data on the thermal conductivity and thermal diffusivity of the solid body is not sufficiently adequate to the physical conditions of the measurements because it does not take into account the heat loss from the heater into the heat insulator and a considerable effect of the contact thermal resistance between the heater and the solid body. Lastly, another serious disadvantage of this method, when used for measuring the thermal conductivity and thermal diffusivity of heterogeneous bodies, consists in the fact that the point temperature sensor is located in one small area (in one point, practically) and responds to the temperature of this small area only. This gives a considerable distortion of the measurement data for the rock which is essentially heterogeneous due to its granularity, fracturing and local variations in the porosity, and makes the measurement data unrepresentative for the total heating area.

There is a known device for measuring the thermal conductivity and thermal diffusivity of solid bodies. It contains a flat sonde 30×90×10 mm in size, which has an internal heat source in the form of thin wires 80, 50 and 30 µm thick and 50 mm long, and three temperature sensors located at a certain distance from the source and used for measuring the temperature gradient between the source center and the distant points of the sonde (Kiyohashi H., Okumura K., Sakaguchi K. and Matsuki K. Development of direct measurement method for thermophysical properties of reservoir rocks in situ by well logging, Proceedings World Geothermal Congress 2000, May 28-Jun. 10, 2000). The sonde is fixed in physical contact with the medium under study. After thermal equilibrium has been reached between the sonde and the medium under study, it is necessary to turn on the heat source and to measure continuously the temperature gradient while introducing corrections for the temperature gradient value in equilibrium. Then, it is necessary to derive the relationship between the temperature gradient measurement data and the observation time and to determine the thermal conductivity and thermal diffusivity of the medium by using the design relationships.

The disadvantages of this device include a low accuracy of measurements in case that the device is used for measuring the thermal conductivity and thermal diffusivity on cylindrical, conical, spherical, elliptical, rough and irregular surfaces, as well as in wells filled with fluid, and the impossibility to achieve a satisfactory thermal contact between the sonde and the medium's wall due to the flat shape of the sonde. Another serious disadvantage of this device includes the distorting effect of the thermal convection of the well fluid, which is possible when the heat from the heater propagates into the surrounding fluid too, thus initiating the convective motion of the fluid and distorting the measurement data. Another disadvantage of this device includes the inconsistency between the theoretical model of the measurement method, developed for using the sonde on flat surfaces of solid bodies, and the real conditions of the measurements taken on solid bodies with non-flat and/or rough or irregular walls. As a result, it is impossible to take into account the effect of the hole wall surface curvature on the thermal conductivity and thermal diffusivity measurement data.

The closest identified analogue of the suggested device is the device used for determining the thermal properties of rock by the flat sonde method, which is based on the regularities of steady-state heat-transfer in a semi-restricted medium on the surface of which a flat heat source is located. The device is described in the article "Flat Sonde Method for Determination of Thermal Properties of Rock in Wells and Mines" by P. I. Filippov, in the book "Methods for Determination of Thermal Properties of Rock", Moscow, Nauka Publishing House, 1970, pages 107-111. The device includes a flat heater, a point temperature sensor, an elastic heat insulator serving as a heater holder, the sonde body to which the elastic heat insulator is attached, and a hold-down unit to press the sonde body to the surface of the solid bodies. The device heats the solid body surface with a flat heater and measures the flat heater temperature during the heater operation. Based on the flat heater temperature data, the thermal conductivity and thermal diffusivity of the solid body is then determined by using the design relationship.

This device has serious disadvantages which reduce considerably the accuracy of the measurements of the solid body's thermal conductivity and thermal diffusivity and narrow considerably its area of application. Such serious disadvantages include an unacceptably low accuracy of the measurements of the solid body's thermal conductivity and thermal diffusivity, taken on cylindrical, conical, spherical, elliptical, rough and irregular surfaces. The same disadvantage applies to the measurements taken in wells, because this device cannot limit the distorting effect of the thermal convection of the well fluid, which occurs when the flat heater is in operation and when the heat is transferred from the flat heater not only to the solid body, but also to the fluid through the heat insulator, the sonde body and the hold-down unit used for holding down the sonde body. Besides, this device is unable to provide the required accuracy level because it does not take into account the effect of the contact thermal resistance on the measurement data. Another considerable disadvantage of the device consists in the fact that it is impossible to take into account the effect of the shape and irregularities of the solid body surface on the results of the measurements of the solid body's thermal conductivity and thermal diffusivity. The disadvantage of this device, when used for measuring the thermal conductivity and thermal diffusivity of heterogeneous bodies, consists in the fact that the point temperature sensor is located in one small area (in one point, practically) and responds to the temperature of this small area only. This gives a considerable distortion of the measurement data for the rock which is essentially heterogeneous due to its granularity, fracturing and local variations in the porosity, and makes the measurement data unrepresentative for the rock volume corresponding to the heating area.

SUMMARY OF THE INVENTION

The technical result achieved through the implementation of the suggested invention consists in a higher accuracy of measurements of the thermal properties of heterogeneous solid bodies, as well of the solid bodies having cylindrical, conical, spherical, elliptical, rough and irregular surfaces, and in wells filled with fluid.

The said technical result is achieved by heating the solid body surface with a heater which is pressed to the solid body surface by using a hold-down element and is equipped with an elastic heat insulator located from the hold-down element side, with the heater being designed as a flexible membrane capable of taking the shape of the solid body surface under the action of the hold-down pressure. Preliminarily, relationships between the calculated thermal conductivity of the solid body and the shape and irregularities of the solid body surface are determined. When the solid body is heated, the heater temperature is measured throughout the heater surface in contact with the solid body. The starting moment of the thermal convection of the ambient medium is determined as the moment when the measurement data start distorting, and the heating is then stopped while the measurements of the heater temperature are continued at the solid body cooling stage, after the heating has been stopped. The thermal conductivity and thermal diffusivity of the solid body are determined, based on the heater temperature measurements data obtained at the solid body heating and cooling stages, by using the pre-determined relationships between the calculated thermal conductivity of the solid body and the shape/irregularities of the solid body surface.

Additional heat-insulator temperature measurements to be taken inside the heat insulator at least in two points located successively in the direction from the heater towards the hold-down element at a known distance from each other will allow to take into account the contact thermal resistance between the heater and the solid body, as well as the heat loss from the heater into the heat insulator.

The heat insulator can be made from a solid material having known thermal conductivity and thermal diffusivity properties, and the surface of the heat insulator side facing the heater has the same shape as the solid body surface where measurements are taken.

The heat insulator can be made from an elastic material capable of taking, under the action of the hold-down pressure, the shape of the solid body surface where measurements are taken. Preliminarily, the relationship between the thermal conductivity of the heat insulator and the shape/size of the heat insulator is determined, the changes in the heat insulator shape and size caused by the action of the hold-down pressure are registered, and the actual thermal conductivity of the heat insulator is established during the measurements of the solid body's thermal properties.

The shape, size and properties of the heat insulator and the hold-down element can be selected in such a way as to prevent the ambient medium from being heated by the heat insulator and/or by the hold-down element and to rule out the possibility of thermal convection of the ambient medium.

Temperature measurements are additionally taken on the heat insulator surface segment or the hold-down element surface segment which is in contact with the ambient medium and which corresponds to the lowest thermal resistance from the heater to the ambient medium (at the ambient medium interface), and when the temperature on the relevant surface segment reaches the value at which thermal convection of the ambient medium occurs at a rate resulting in an increased inaccuracy of measurements of the solid body's thermal properties, the heating of the solid body is stopped.

The device used for measuring the thermal properties of solid bodies includes a heater and a temperature sensor which are designed as one flexible membrane that serves as a heater and as a temperature sensor at the same time and is capable of taking, under the action of the hold-down pressure, the shape of the solid body surface. From one side, the membrane is equipped with a heat insulator and a hold-down element which is used for pressing it to the solid body surface. Due to its flexibility, the heater is capable of taking, under the action of the hold-down pressure, the shape of the solid body surface with all its irregularities. The device additionally contains a unit which is connected to the heater and is used for turning the heater on and off and for registering, processing and correcting the electric signal of the heater temperature. The said unit is provided with algorithms for processing and correcting the electric signal and for calculating the solid body's thermal conductivity and thermal diffusivity adjusted for the shape and irregularities of the solid body surface, based on the pre-determined relationships.

The heat insulator can be equipped with at least two heat insulator temperature sensors which are located successively in the direction from the heater towards the hold-down element at a known distance from each other. The device is equipped with an additional electronic unit which is connected to the heat insulator temperature sensors and is used for registering and processing the signals from the said sensors.

The heat insulator can be made from a solid material having known thermal conductivity and thermal diffusivity, and its side facing the heater has the same shape as the solid body surface where measurements are taken.

The heat insulator is made from an elastic material which is capable of taking, under the action of the hold-down pressure, the shape of the solid body surface where measurements are taken, and which has a known relationship between the thermal conductivity and the shape/size of the heat insulator.

The heat insulator can be equipped with at least one sensor to be used for detecting the changes in the heat insulator shape and size, caused by the action of the hold-down pressure during the measurements of the solid body's thermal properties.

An additional temperature sensor can be installed on the heat insulator surface or the hold-down element surface (in the area where the heat insulator or the hold-down element contacts the ambient medium and where the lowest thermal resistance from the heater to the ambient medium is observed), and this sensor is connected to the additional electronic unit which will register the signal coming from the additional temperature sensor, and will record the moment when the signal from the additional temperature sensor reaches the allowable specified value, and will turn the heater off immediately after the signal from the additional temperature sensor has exceeded this allowable value.

Additional temperature sensors can be installed on the heat insulator surface and the hold-down element surface (in the area where the heat insulator and the hold-down element contact the ambient medium), and these sensors are connected to the additional electronic unit which will register the signals coming from the additional temperature sensors, and will record the moment when the signal from at least one of the additional temperature sensors reaches the allowable specified value, and will turn the heater off immediately after the signal from at least one of the additional temperature sensors has exceeded this allowable value.

The heat insulator and the hold-down element can have such shapes, sizes and thermal properties that rule out the possibility of thermal convection of the ambient medium.

DETAILED DESCRIPTION OF THE PREFERRED EMBODIMENTS

The invention is clarified by a drawing which schematically shows the device described in this invention and used for determining the thermal properties of the solid body in accordance with the suggested method (FIG. 1).

The device includes heater 2 designed as a flexible membrane which serves as a heater and as a temperature sensor at the same time and registers the temperature of heater 2 throughout the heater surface. Such a flexible membrane to be used as heater 2 can be manufactured, for example, by etching thin metal foil applied on a thin flexible insulator or covered with thin flexible insulators from both sides. Heater 2 manufactured in this way is capable of taking, under the action of the hold-down pressure, the shape of the surface of solid body 1 under study, in case that the solid body has a cylindrical, conical, spherical or elliptical surface, as well as a rough or irregular surface.

To transfer the hold-down pressure to heater 2 to give it the shape of the solid body surface, and to insulate heater 2 from hold-down element 5 and from ambient medium 10 (e.g. fluid) during the measurements taken in a well filled with fluid, the device includes heat insulator 3 which mechanically contacts heater 2. Heat insulator 3 is manufactured in such a way as to ensure that its side facing the heater has the same shape as the solid body surface during the measurements. To provide the required hold-down pressure to press heat insulator 3 to heater 2, the device includes hold-down element 5 which mechanically contacts heat insulator 3.

Temperature sensors 4 for heat insulator 3 can be installed inside heat insulator 3 at least in two points located successively in the direction from heater 2 towards hold-down element 5 at a known distance from each other.

The device includes electronic unit 7 which is used for turning heater 2 on and off and for registering, processing and correcting the heater temperature signal both in the time range from the start of the heating of solid body 1 with heater 2 to the start of the thermal convention of the ambient medium and after the termination of the heating of solid body 1. To process data on the temperature of heater 2 and to determine the thermal conductivity and thermal diffusivity of solid body 1, it is necessary to enter the pre-determined relationships between the calculated thermal conductivity and the shape and irregularities of the surface of solid body 1 into unit 7 prior to heating. Electronic unit 7 is connected to heater 2. Preliminarily, the algorithm for processing and adjusting the signal of heater 2 for the shape and irregularities of the solid body surface should be entered into electronic unit 7 to be used for processing and correcting the electric signal of the heater temperature and for calculating the thermal conductivity and thermal diffusivity of solid body 1, which will allow you to determine the thermal conductivity and thermal diffusivity of solid body 1, adjusted for the shape and irregularities of the solid body surface.

Unit 8 included into the device is designed to register and to process the signals from temperature sensors 4 inside heat insulator 3, as well as to calculate the temperature gradient inside heat insulator 3 and the heat flow from heater 2 to heat insulator 3. To calculate the heat flow from heater 2 to heat insulator 3, it is necessary to enter data on the thermal conductivity of the material of heat insulator 3 and on the distances between temperature sensors 4 inside heat insulator 3, into unit 8. Unit 8 is connected to temperature sensors 4 inside heat insulator 3.

Additional temperature sensor 6 to be used for measuring the temperature at the interface between ambient medium 10 and heat insulator 3 or hold-down element 5 can be installed on the external surface of heat insulator 3 or hold-down element 5 in the area corresponding to the minimum thermal resistance from heater 2 to ambient medium 10.

The device also includes electronic unit 9 to be used for registering and processing the signals from temperature sensor 6, which is connected to additional temperature sensor 6 and unit 7. Unit 9 is designed to register and to process the signals from additional temperature sensor 6. In case that the signal from additional temperature sensor 6 reaches the allowable specified value, unit 9 generates a heating termination signal and transmits this signal to unit 7. Unit 7 then turns heater 2 off and so stops the heating of solid body 1 to ensure that thermal convection of ambient medium 10 will not affect the results of the measurements of the thermal properties of solid body 1.

In one of its embodiments, heat insulator 3 is made of a solid material having known thermal conductivity properties. The side of heat insulator 3, facing heater 2, is given the shape of the surface of solid body 3, where measurements are taken.

Heat insulator 3 and hold-down element 5 can have such pre-selected shapes, sizes and thermal properties that rule out the possibility of thermal convection of ambient medium 10.

Also, we suggest an embodiment where heat insulator 3 is made from an elastic material, which allows heat insulator 3 to take, under the action of the pressure of hold-down element 5, the shape of the surface of solid body 1. One or more electromechanical sensors 11 can be additionally installed on heat insulator 3, and they will register the shape and size of heat insulator 3 when under the action of the pressure of hold-down element 5, and will transmit data on the shape and size of heat insulator 3 to unit 8 during the measurements of the thermal conductivity and thermal diffusivity of solid body 1.

The device can also include a few additional temperature sensors 6 which are installed in a few points in the areas of contact of heat insulator 3 and hold-down element 5 with ambient medium 10. Additional temperature sensors 6 are connected to unit 9 which registers the signals from additional temperature sensors 6 and records the moment when the signal from at least one of additional temperature sensors 6 reaches the allowable specified value. Unit 9 generates a heating termination signal and transmits this signal to unit 7. Unit 7 then turns heater 2 off and so stops the heating of solid body 1 to ensure that thermal convection of ambient medium 10 will not affect the results of the measurements of the thermal conductivity and thermal diffusivity of solid body 1.

Heater 2, which is used in the suggested method and is designed as a flexible membrane capable of taking the shape of the surface of solid body 1, provides constant thermal resistance between heater 2 and the surface of solid body 1 and, consequently, stable heat-flux density from heater 2 to solid body 1 during the measurements of the thermal properties of heterogeneous solid body 1 in case that solid body 1 has a cylindrical, conical, spherical, elliptical, and/or rough or irregular surface, and in case that the thermal properties of the solid body are measured in a well filled with fluid.

Preliminarily, relationships between the calculated thermal conductivity of solid body 1 and the shape and irregularities of the solid body surface are determined. During the measurements, the shape of heater 2 should be changed in such a way as to fit the shape and irregularities of the surface of solid body 1, so that perfect thermal contact could be achieved between flexible heater 2 and solid body 1 throughout the surface of heater 2. This approach to the contact to be achieved between heater 2 and solid body 1 ensures that temperatures will be simultaneously registered throughout the contact surface of heater 2 and solid body 1. The registration of the temperature of heater 2 throughout the heater surface in contact with solid body 1 gives representative data on the temperature of heater 2 for the entire area of solid body 1 in contact with entire heater 2, not only data on the temperature in one small area of solid body 1, which may occasionally coincide with a separate segment of solid body 1, containing a grain or a fracture and being unrepresentative in terms of its thermal properties.

When solid body 1 is heated by heater 2, the temperature difference is measured by using temperature sensors 4 inside heat insulator 3 at least in two points located successively in the direction from heater 2 towards hold-down element 5 at a known distance from each other. After heater 2 has been installed on the surface of solid body 1, the distances between heat insulator temperature sensors 4 are measured. After the temperature difference between sensors 4 has been measured for the steady-state heating conditions, and data on the measured distances between temperature sensors 4 and on the thermal conductivity of heat insulator 3 have been obtained for these conditions, the density of the heat flux of the loss and the total heat flux of the loss from heater 2 into heat insulator 3 are determined by using a Fourier equation. The evaluation of the heat flux from heater 2 to heat insulator 3 is required because the design formula to be used for determining the thermal conductivity includes the power to be transferred to solid body 1 from heater 2 when solid body 1 is heated. This power is defined as the total electric power delivered to heater 2 from an external current source. If a considerable portion of this power is not actually transferred, as the useful power, to solid body 2 but is uncontrollably lost for heating heat insulator 3, this will result in a serious inaccuracy of measurements of the thermal conductivity of solid body 1.

Additional temperature sensor 6 to be installed on the external surface of heat insulator 3 or hold-down element 5 in the area of the lowest thermal resistance from heater 2 to ambient medium 10 is used for determining the temperature of heat insulator surface or hold-down element surface in contact with ambient medium 10. Unit 9 intended for processing the signal from temperature sensor 6 is used for picking up the signal from temperature sensor 6, corresponding to the critical temperature of heat insulator surface or hold-down element surface in contact with ambient medium 10. The critical temperature of sensor 6 corresponds to the beginning of the convection of ambient medium 10, which distorts the conditions of the measurements of the thermal conductivity and thermal diffusivity of solid body 1. That is why unit 9 intended for processing the signal from temperature sensor 6 processes the signal from temperature sensor 6 in such a way as to generate a heating termination signal, and transmits this signal to unit 7. Unit 7 then turns heater 2 off and so stops the heating of solid body 1. After the electric power supply to heater 2 has been discontinued, the registration of the heater temperature is still continued, and the thermal conductivity and thermal diffusivity of the solid body 1 are then determined by processing the data on the temperature of heater 2 both in the time range from the start of the operation of heater 2 to the start of the thermal convention of ambient medium 10 and after the termination of the heating of solid body 1 with heater 2.

For measurement accuracy improvement purposes, the side of solid-material heat insulator 3, facing heater 2, should be preliminarily given (by mechanical treatment or heat-treatment) the shape of the surface of solid body 1, where measurements will be taken. Since the evaluation of the heat loss from heater 2 into heat insulator 3 requires data on the thermal conductivity of heat insulator 3, it is necessary to determine and to record the thermal conductivity of the material of heat insulator 3 prior to taking the measurements.

It is also possible to manufacture heat insulator 3 from an elastic material. This will allow you to use heat insulator 3 capable of taking (under the action of the pressure of hold-down element 5) the shape of the surface of solid body 1 where measurements are taken, to press heater 2 to solid body 1 having a cylindrical, conical, spherical, elliptical, and/or rough or irregular surface, as well as in wells filled with ambient medium 10. In this case, it is necessary to pre-determine the relationship between the thermal conductivity of elastic heat insulator 3 and the shape/size of heat insulator 3. For this purpose, it is necessary to register the changes in the shape and size of elastic heat insulator 3, caused by the action of the pressure of hold-down element 5. As the shape and the size of heat insulator 3 change, it is necessary to take repeated measurements of the thermal conductivity of heat insulator 3, thus determining the actual thermal conductivity of heat insulator 3 for each combination of its shape and size. The resulting data on the thermal conductivity of heat insulator 3 are used for determining the thermal conductivity and thermal diffusivity of the solid body during the measurements.

Another additional way to increase the accuracy of measurements of thermal properties of solid body 1 by eliminating the heat loss from heater 2, caused by the convection of ambient medium 10, is to preselect the shape, size and properties of heat insulator 3 and hold-down element 5 in such a way as to totally prevent ambient medium 10 from being heated by heat insulator 3 and/or hold-down element 5 and, consequently, to rule out the possibility of thermal convection of ambient medium 10.

The measurement accuracy which is increased by eliminating the heat loss from heater 2, caused by the convection of ambient medium 10, is also improved due to temperature measurements taken by additional temperature sensor 6 on the segment of the surface of heat insulator 3 or hold-down element 5, which corresponds to the lowest thermal resistance from heater 3 to ambient medium 10 (at the ambient medium interface). These measurement data are used as a basis for determination of the time moment when the temperature on a segment of the surface of heat insulator 3 or hold-down element 5 reaches the value at which thermal convection of ambient medium 10 occurs at a rate resulting in an increased inaccuracy of measurements of the thermal conductivity and thermal diffusivity of solid body 1.

As an example of the application of the suggested method for determination of thermal properties of solid bodies, we can consider the case where it is necessary to determine the thermal conductivity and thermal diffusivity of a solid body having a cylindrical surface the curvature radius of which is equal to 100 mm. For this purpose, a device for measuring the thermal properties of solid bodies is used, and it includes a thin flexible membrane in the form of a spiral which has a turn width 0.02 mm and a pitch of 0.03 mm and is made of brass foil 0.01 mm thick and is placed on the surface of a rectangle 15×30 mm in size. Two potential tap-offs are attached to the ends of the spiral so that the spiral resistance could be determined during the spiral heating. One surface of the membrane is open, and a flexible heat insulator made of sponge rubber 20 mm thick is placed along the other surface. There is a plate located on the opposite side of the sponge rubber, and this plate is a component of the hold-down element. Prior to determining the thermal properties of the solid body, it is necessary to determine the relationship between the brass spiral resistance and temperature. Given that that the heater is not a flat heat source as provided for in the design formulas for the thermal conductivity and thermal diffusivity of the solid body but has the shape of a cylinder with the curvature radius of 100 mm, the value of the correction to be introduced into the formulas for the thermal conductivity and thermal diffusivity of the solid body is established by using the available design relationships and experimental data. Prior to determining the thermal properties, it is necessary to press the flexible membrane to the solid body surface by using the elastic heat insulator and the hold-down element, so that the flexible membrane could fully fit the cylindrical surface of the solid body. In order to determine the thermal properties of the solid body, it is necessary to supply voltage to the membrane to heat it up, and to start at the same time the determination of the membrane temperature from the membrane resistance during the membrane heating. When the temperature of the external surface of the hold-down element in contact with the ambient medium reaches the specified limit corresponding to the beginning of the distorting effect the thermal convection of the ambient medium has on the measurement data, it is necessary to discontinue the voltage supply to the flexible membrane, thus terminating the flexible membrane heating process. The registration of the flexible membrane temperature is continued at the flexible membrane cooling stage. The flexible membrane temperature values determined both at the flexible membrane heating stage before the specified time moment when the convection of the ambient medium started affecting the measurement data, and at the flexible membrane cooling stage, are substituted in the design formulas for the thermal conductivity and thermal diffusivity of the solid body, together with the pre-determined corrections allowing for the difference between the actual solid body surface and a flat surface. Based on the design formulas and the pre-determined corrections, the thermal conductivity and thermal diffusivity of the solid body having a cylindrical surface is determined.

The invention claimed is:

1. A method for determination of thermal properties of a solid body, comprising the following steps:
   predetermining relationships between the calculated thermal conductivity of the solid body and the shape and irregularities of the solid body surface;
   providing a thermal contact between the solid body and a heater equipped with a hold-down element and a heat insulator located from the hold-down element side, the heater made in the form of a flexible membrane capable of taking the shape of the solid body surface under the action of the hold-down pressure and additionally serving as a temperature sensor, over the entire heater surface by changing the heater shape in such a way as to ensure that it fits the shape and irregularities of the solid body surface;
   heating the solid body with the heater and registering the heater temperature during the heating throughout the entire heater surface in contact with the solid body;
   determining a starting moment of thermal convection of the ambient medium as the moment when the measurement data start distorting,
   stopping the heating and continuing registration of the heater temperature,
   determining thermal conductivity and thermal diffusivity of the solid body by processing the heater temperature measurement data both in the time range from the start of the solid body heating process to the start of the thermal convention of the ambient medium and after the termination of the solid body heating process, with the heater temperature measurement data being processed and the thermal conductivity and thermal diffusivity of the solid body being determined by using the pre-determined relationships between the calculated thermal conductivity and the shape and irregularities of the solid body surface.

2. A method of claim 1, wherein the heat-insulator temperature is being additionally measured inside the heat insulator at least in two points located successively in the direction from the heater to the hold-down element at a known distance from each other.

3. A method of claim 1, wherein the heat insulator is made from a solid material having known thermal conductivity and thermal diffusivity, and the surface of the heat insulator side facing the heater has the same shape as the solid body surface where measurements are taken.

4. A method of claim 1, wherein the heat insulator is made of an elastic material capable of taking, under the action of the hold-down pressure, the shape of the solid body surface where measurements are taken.

5. A method of claim 4, wherein the relationship between the thermal conductivity of the heat insulator and the shape and size of the heat insulator is pre-determined, the changes in the heat insulator shape and size caused by the action of the hold-down pressure are registered, and the actual thermal conductivity of the heat insulator is established during the measurements of the solid body's thermal properties.

6. A method of claim 1, wherein the shape, size and properties of the heat insulator and the hold-down element are selected in such a way as to prevent heating of the ambient medium by the heat insulator and/or by the hold-down element and thermal convection of the ambient medium.

7. A method of claim 1, wherein temperature measurements are taken on the heat insulator surface segment or the hold-down element surface segment which is in contact with the ambient medium and which corresponds to the lowest thermal resistance from the heater to the ambient medium at the ambient medium interface, and when the temperature on the relevant surface segment reaches the value at which thermal convection of the ambient medium occurs at a rate resulting in an increased inaccuracy of measurements of the solid body's thermal properties, the heating of the solid body is stopped.

8. A method of claim 1, wherein temperature measurements are taken on the heat insulator surface segments and the hold-down element surface segments which are in contact with the ambient medium and which correspond to the lowest thermal resistance from the heater to the ambient medium at the ambient medium interface, and when the temperature on the heat insulator surface segment or the hold-down element surface segment reaches the value at which thermal convection of the ambient medium occurs at a rate resulting in an increased inaccuracy of measurements of the solid body's thermal properties, the heating of the solid body is stopped.

9. A device for measuring the thermal properties of a solid body comprising:
a heater equipped with a heat insulator and a hold-down element from one side, and a heater temperature sensor made as one flexible membrane that serves as a heater and as a temperature sensor at the same time and is capable of taking, under the action of the hold-down pressure, the shape of the solid body surface;
a unit which is connected to the heater and is used for turning the heater on and off and for registering, processing and correcting the electric signal of the heater temperature, and this unit for turning the heater on and off and for registering, processing and correcting the electric signal of the heater temperature is provided with algorithms for processing and correcting the electric signal and for calculating the solid body's thermal conductivity and thermal diffusivity adjusted for the shape and irregularities of the solid body surface, based on a pre-determined relationships.

10. A device of claim 9, wherein the heat insulator is equipped with at least two heat insulator temperature sensors located successively in the direction from the heater towards the hold-down element at a known distance from each other and with an additional electronic unit connected to the heat insulator temperature sensors and used for registering and processing the signals from the heat insulator temperature sensors.

11. A device of claim 9, wherein the heat insulator is made from a solid material having known thermal conductivity, and the surface of the heat insulator side facing the heater has the same shape as the solid body surface where measurements are taken.

12. A device of claim 9, wherein the heat insulator is made from an elastic material capable of taking, under the action of the hold-down pressure, the shape of the solid body surface where measurements are taken.

13. A device of claim 12, wherein the heat insulator is equipped with at least one sensor to be used for detecting the changes in the heat insulator shape and size, caused by the action of the hold-down pressure during the measurements of the solid body's thermal properties.

14. A device of claim 9, wherein an additional temperature sensor is installed on the heat insulator surface or the hold-down element surface in the area where the heat insulator or the hold-down element contacts the ambient medium and where the lowest thermal resistance from the heater to the ambient medium is observed, and this sensor is connected to the additional electronic unit which will register the signal coming from the additional temperature sensor, and will record the moment when the signal from the additional temperature sensor reaches the allowable specified value, and will turn the heater off immediately after the signal from the additional temperature sensor has exceeded this specified value.

15. A device of claim 9, wherein additional temperature sensors are installed on the heat insulator surface and the hold-down element surface in the area where the heat insulator and the hold-down element contact the ambient medium, and these sensors are connected to the additional electronic unit which will register the signals coming from the additional temperature sensors, and will record the moment when the signal from at least one of the additional temperature sensors reaches the allowable specified value, and will turn the heater off immediately after the signal from at least one of the additional temperature sensors has exceeded this allowable specified value.

16. A device of claim 9, wherein the heat insulator and the hold-down element have such shapes, sizes and thermal properties that rule out the possibility of thermal convection of the ambient medium.

* * * * *